(12) United States Patent
Endo et al.

(10) Patent No.: US 10,304,158 B2
(45) Date of Patent: May 28, 2019

(54) IMAGE PROCESSING APPARATUS, IMAGE PROCESSING METHOD AND NON-TRANSITORY COMPUTER-READABLE MEDIUM WITH CALCULATION OF INFORMATION REPRESENTING DIRECTION OF TARGET TISSUE AND WITH ESTIMATING OF DEPICTING APPEARANCE OF TARGET TISSUE

(71) Applicant: CANON KABUSHIKI KAISHA, Tokyo (JP)

(72) Inventors: Takaaki Endo, Urayasu (JP); Kiyohide Satoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 2 days.

(21) Appl. No.: 15/224,854

(22) Filed: Aug. 1, 2016

(65) Prior Publication Data

US 2017/0039776 A1 Feb. 9, 2017

(30) Foreign Application Priority Data

Aug. 6, 2015 (JP) ................. 2015-156241

(51) Int. Cl.
*G06T 3/00* (2006.01)
*G06T 7/00* (2017.01)
*G06T 11/00* (2006.01)
*G06F 19/00* (2018.01)

(52) U.S. Cl.
CPC .......... *G06T 3/0068* (2013.01); *G06F 19/321* (2013.01); *G06T 3/0093* (2013.01); *G06T 7/0016* (2013.01); *G06T 11/008* (2013.01); *G06T 2207/10081* (2013.01); *G06T 2207/10088* (2013.01); *G06T 2207/20221* (2013.01);

(Continued)

(58) Field of Classification Search
CPC ..... G06T 15/503; G06T 19/20; G06T 3/0068; G06T 7/30; G06T 2207/10088; G06T 2207/20221; G06T 2207/30101
See application file for complete search history.

(56) References Cited

U.S. PATENT DOCUMENTS 6,106,466 A * 8/2000 Sheehan ............ A61B 5/1075
128/916
6,792,370 B2 9/2004 Satoh et al.
6,993,450 B2 1/2006 Takemoto et al.
(Continued)

FOREIGN PATENT DOCUMENTS

JP 2009-268741 A 11/2009

OTHER PUBLICATIONS

Wein, Wolfgang, et al. "Automatic CT-ultrasound registration for diagnostic imaging and image-guided intervention." Medical image analysis 12.5 (2008): 577-585.*

(Continued)

*Primary Examiner* — Daniel F Hajnik
(74) *Attorney, Agent, or Firm* — Venable LLP (57) ABSTRACT

An image processing apparatus acquires information representing directivity at the time of imaging a first image of an object obtained by a first apparatus, extracts an image of a target tissue from a second image of the object obtained by a second apparatus, and estimates a depicting appearance of the target tissue in the first image based on a relationship between the information representing the directivity and the image of the target tissue.

17 Claims, 8 Drawing Sheets

(52) U.S. Cl.
CPC ............... *G06T 2207/30096* (2013.01); *G06T 2207/30101* (2013.01)

(56) References Cited

U.S. PATENT DOCUMENTS

| | | | |
|---|---|---|---|
| 7,092,109 B2 | 8/2006 | Satoh et al. | |
| 7,130,754 B2 | 10/2006 | Satoh et al. | |
| 7,446,768 B2 | 11/2008 | Satoh et al. | |
| 7,626,596 B2 | 12/2009 | Kotake et al. | |
| 9,324,148 B2 | 4/2016 | Ishikawa et al. | |
| 2009/0063118 A1* | 3/2009 | Dachille | G06F 17/30262 703/11 |
| 2012/0069049 A1* | 3/2012 | Howe | G06T 7/0012 345/629 |
| 2012/0143090 A1* | 6/2012 | Hay | A61B 6/505 600/587 |
| 2015/0070469 A1 | 3/2015 | Yoshibayashi et al. | |
| 2015/0110373 A1* | 4/2015 | Shaham | G06T 7/0081 382/131 |
| 2016/0027179 A1 | 1/2016 | Takama et al. | |
| 2016/0042248 A1 | 2/2016 | Endo et al. | |
| 2016/0125605 A1* | 5/2016 | Lee | G06T 11/008 382/131 |

OTHER PUBLICATIONS

Nam, Woo Hyun, et al. "Automatic registration between 3D intra-operative ultrasound and pre-operative CT images of the liver based on robust edge matching." Physics in medicine and biology 57.1 (2011): 69.*

Lee, Duhgoon, et al. "Non-rigid registration between 3D ultrasound and CT images of the liver based on intensity and gradient information." Physics in medicine and biology 56.1 (2010): 117.*

De La Zerda, Adam, et al. "A brain tumor molecular imaging strategy using a new triple-modality MRI-photoacoustic-Raman nanoparticle." SPIE BiOS. International Society for Optics and Photonics, 2013.*

King, Andrew P., et al. "Registering preprocedure volumetric images with intraprocedure 3-D ultrasound using an ultrasound imaging model." IEEE Transactions on Medical Imaging 29.3 (2010): 924-937.*

Wein, Wolfgang et al., "Simulation and Fully Automatic Multimodal Registration of Medical Ultrasound", Medical Image Computing and Computer-Assisted Intervention—MICCAI, 2007, pp. 136-143, vol. 4791 of Lecture Notes in Computer Science, Springer.

* cited by examiner

PAT APPARATUS
COORDINATE SYSTEM $C_{PAT}$

FIG. 12

PAT APPARATUS COORDINATE SYSTEM $C_{PAT}$

IMAGE PROCESSING APPARATUS, IMAGE
PROCESSING METHOD AND
NON-TRANSITORY COMPUTER-READABLE
MEDIUM WITH CALCULATION OF
INFORMATION REPRESENTING
DIRECTION OF TARGET TISSUE AND
WITH ESTIMATING OF DEPICTING
APPEARANCE OF TARGET TISSUE

BACKGROUND OF THE INVENTION

Field of the Invention

The present invention relates to an image processing apparatus for presenting a three-dimensional tomographic image, an image processing method, and a non-transitory computer-readable storage medium.

Description of the Related Art

In the medical field, a doctor performs diagnosis by using medical images obtained by various types of modalities such as an MRI (Magnetic Resonance Imaging) apparatus, ultrasonic diagnostic apparatus, PAT (PhotoAcoustic Tomography) apparatus, and X-ray CT (Computer Tomography) apparatus. Depending on the modality or imaging mode to be used, a target tissue is sometimes depicted as if it had a defect, in spite of the fact that the target tissue has no defect (that is, a pseudo defective portion). Japanese Patent Laid-Open No. 2009-268741 discloses a method of extracting a pseudo defective portion of a target tissue which occurs when obtaining a medical image, performing interpolation based on information representing the direction of the target tissue, and displaying the resultant image.

In addition, the doctor sometimes performs diagnosis by using medical images obtained by various types of modalities or sometimes performs diagnosis by comparing images obtained by the same modality with different imaging modes, different imaging body postures, different phases, different imaging dates, and the like. In such a case as well, owing to the influence of directivity at the time of imaging, the depicting appearance of the same tissue sometimes differs depending on a target image (one of images to be compared) and a reference image (the other image to be compared). A technique of estimating the depicting appearance of a target image with directivity at the time of imaging based on a reference image and presenting the resultant image is disclosed in W. Wein, A. Khamene, D-A. Clevert, O. Kutter, and N. Navab, "Simulation and fully automatic multimodal registration of medical ultrasound", Proc. MIC-CAI' 07, vol. 1, pp. 136-143, 2007.

The method disclosed in Japanese Patent Laid-Open No. 2009-268741 does not necessarily provide proper interpolation when a pseudo defective portion in which no target tissue is depicted ranges widely. The method disclosed in W. Wein. et al. does not perform processing based on a target tissue, and hence cannot properly estimate the depicting appearance of the target tissue in a target image.

SUMMARY OF THE INVENTION

According to one aspect of the present invention, there is provided an image processing apparatus which comprises: an acquisition unit configured to acquire information representing directivity at the time of imaging a first image of an object obtained by a first apparatus; an extraction unit configured to extract an image of a target tissue from a second image of the object obtained by a second apparatus; and an estimation unit configured to estimate a depicting appearance of the target tissue in the first image based on a relationship between the information representing the directivity and the image of the target tissue.

Further features of the present invention will become apparent from the following description of exemplary embodiments (with reference to the attached drawings).

DESCRIPTION OF THE EMBODIMENTS

Embodiments of the present invention will be described in detail below with reference to the accompanying drawings. Note however that the scope of the present invention is not limited to the examples shown in the accompanying drawings.

(First Embodiment)

An image processing apparatus according to this embodiment estimates the depicting appearance of a target tissue in a target image (one of images to be compared) based on information representing the direction of the target tissue in a reference image of an object. A depicting appearance expresses the manner of how a target tissue is depicted as an image. The image processing apparatus then changes the displaying appearance of a reference image of the target tissue (the other image to be compared) based on the estimated depicting appearance. The displaying appearance indicates a visually expressed state. Note that in the embodiment, an object is imaged by different modalities, and the obtained images are called a target image (to be also referred to as the first image hereinafter) and a reference image (to be also referred to as the second image hereinafter), respectively. In addition, in the embodiment, in the following description, the object is the breast, a target image (first image) is a PAT image (an image obtained by a PAT apparatus), a reference image (second image) is an MRI image (an image obtained by an MRI apparatus), and a target tissue is a blood vessel.

Figure 1:
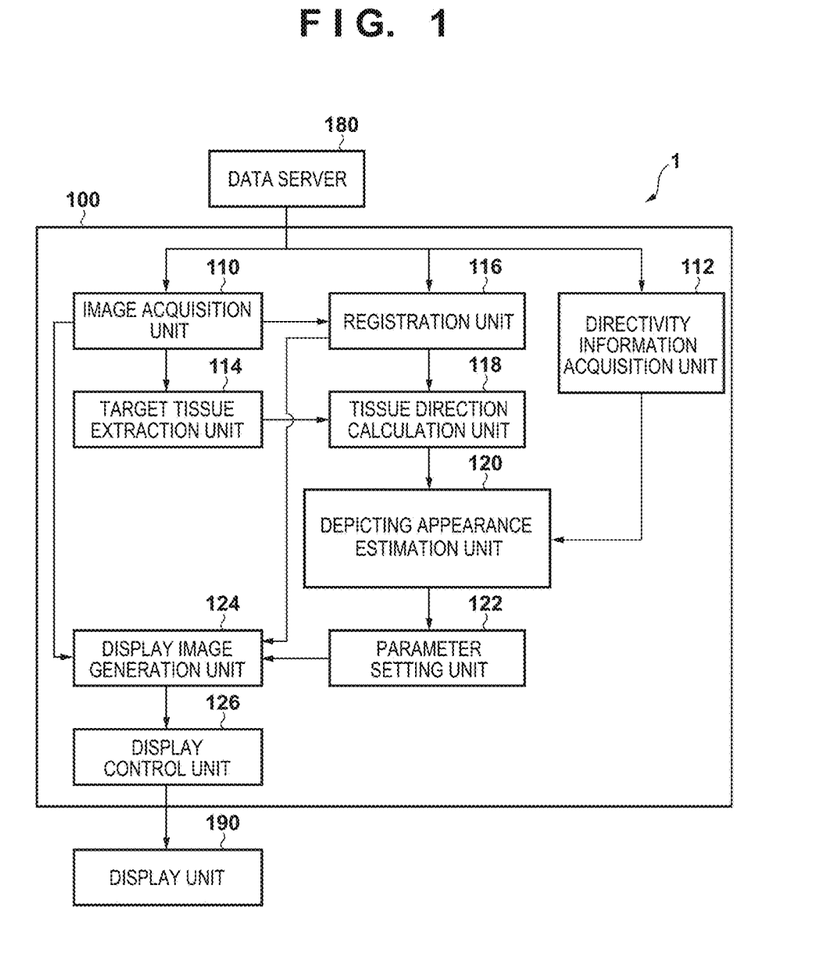
FIG. 1 is a block diagram showing the functional arrangements of an image processing system and an image processing apparatus according to the first embodiment.

FIG. 1 shows the arrangement of an image processing system 1 according to this embodiment. As shown in FIG. 1, the image processing system 1 according to the embodiment includes a data server 180, an image processing apparatus 100, and a display unit 190. Note however that the constituent elements of the image processing system 1 are not limited to these devices and the like, and may further include other constituent elements, or some of them may be excluded.

The data server 180 holds the first and second images of an object. In addition, the data server 180 holds registration information between the first and second images. The data server 180 outputs these pieces of information to the image processing apparatus 100 in accordance with a request from the image processing apparatus 100.

Registration information between the first and second images is information as a clue to registration or a registration result. For example, as the former (information as a clue to registration), the data server 180 holds the three-dimensional coordinates of a corresponding point group of a branch portion or the like of a blood vessel structure commonly depicted in the first and second images. Corresponding points may be manually input by a doctor or technician, or acquired by image processing. In addition, as the latter (registration result), the data server 180 holds rigid-body transformation parameters between the images, affine transformation parameters, nonlinear deformation model parameters, deformation fields, and the like. These pieces of information are derived in advance by using another image processing apparatus (not shown) which performs association and registration between the images. The display unit 190 displays an image output from the image processing apparatus 100.

The image processing apparatus 100 includes an image acquisition unit 110, a directivity information acquisition unit 112, a target tissue extraction unit 114, a registration unit 116, a tissue direction calculation unit 118, a depicting appearance estimation unit 120, a parameter setting unit 122, a display image generation unit 124, and a display control unit 126. The image processing apparatus 100 is connected to the data server 180 and the display unit 190.

The image acquisition unit 110 acquires the first and second images of an object from the data server 180. The directivity information acquisition unit 112 acquires information representing directivity at the time of imaging the first image of the object imaged by the first apparatus. The target tissue extraction unit 114 extracts an image of a target tissue (a blood vessel in this embodiment) from the second image of the object imaged by the second apparatus. Note that in the embodiment, the first apparatus is a PAT apparatus, and the second apparatus is an MRI apparatus. The registration unit 116 acquires a deformation rule to deform the second image to the first image, and deforms the second image toward the first image by using the deformation rule, thereby generating a deformed image of the second image. The tissue direction calculation unit 118 calculates information representing the direction of the target tissue (blood vessel running information in the embodiment) based on an image of the target tissue. The depicting appearance estimation unit 120 estimates the depicting appearance of the target tissue in the first image based on the relationship between the information representing the directivity and the image of the target tissue. The parameter setting unit 122 sets display parameters for the generation of a display image. The display image generation unit 124 generates a display image from the first and second images based on the parameters set by the parameter setting unit 122. The display control unit 126 performs control to display the generated display image on the display unit 190.

Figure 2:
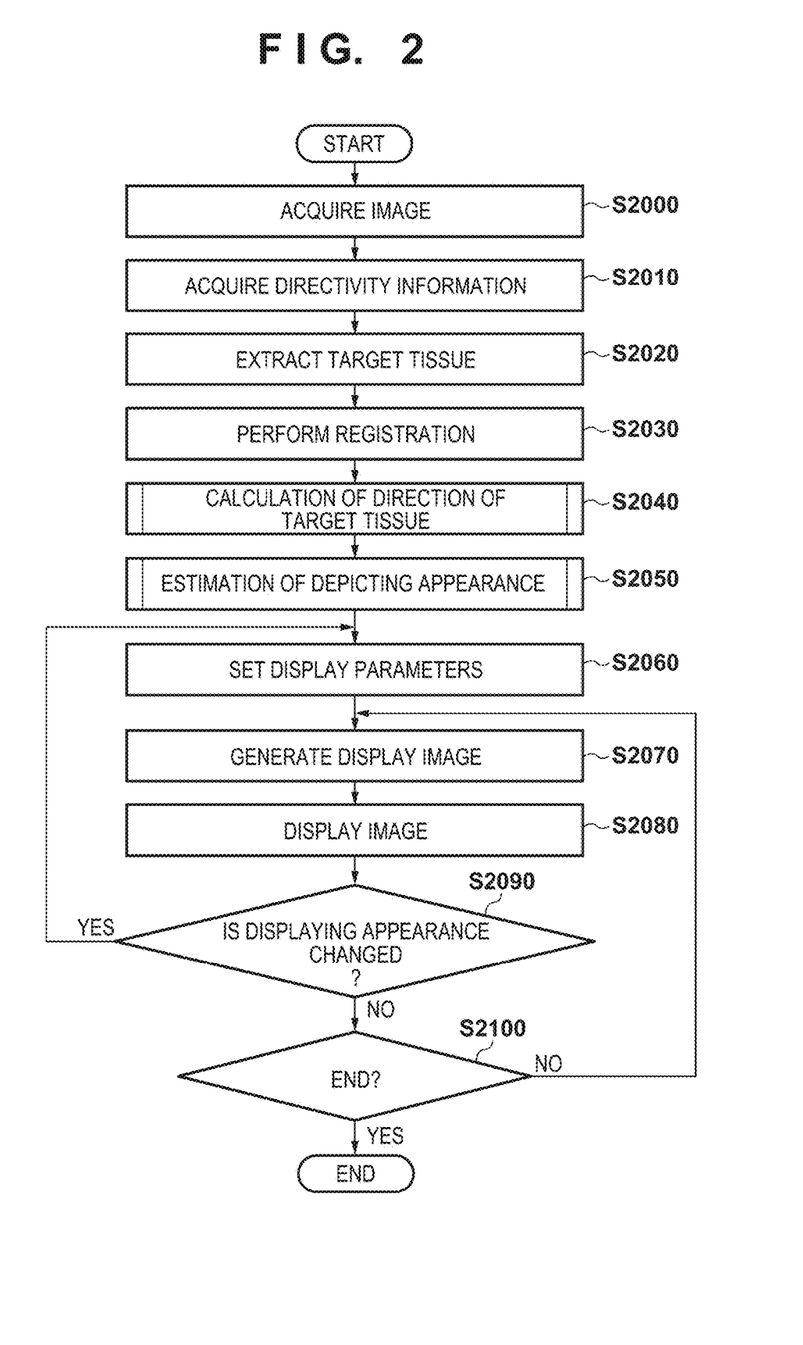
FIG. 2 is a flowchart showing a processing procedure performed by the image processing apparatus according to the first embodiment.

A processing procedure executed by the image processing apparatus 100 according to this embodiment will be described next with reference to the flowchart of FIG. 2.

(S2000: Acquisition of Image)

In step S2000, the image acquisition unit 110 acquires the first and second images of the object from the data server 180.

(S2010: Acquisition of Directivity Information)

In step S2010, the directivity information acquisition unit 112 acquires information (directivity information) representing directivity at the time of imaging the first image from the data server 180. In this embodiment, the directivity information acquisition unit 112 acquires, as information representing directivity, direction information (direction vector) representing the direction of the directivity and angle information (the scalar value of the angle) representing the strength of the directivity.

Figure 11:
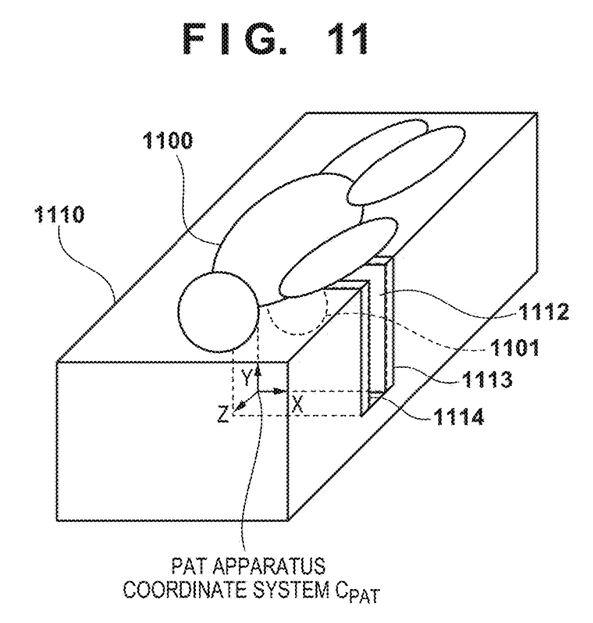
FIG. 11 is a view showing an example of an imaging apparatus according to the first embodiment.
Figure 12:
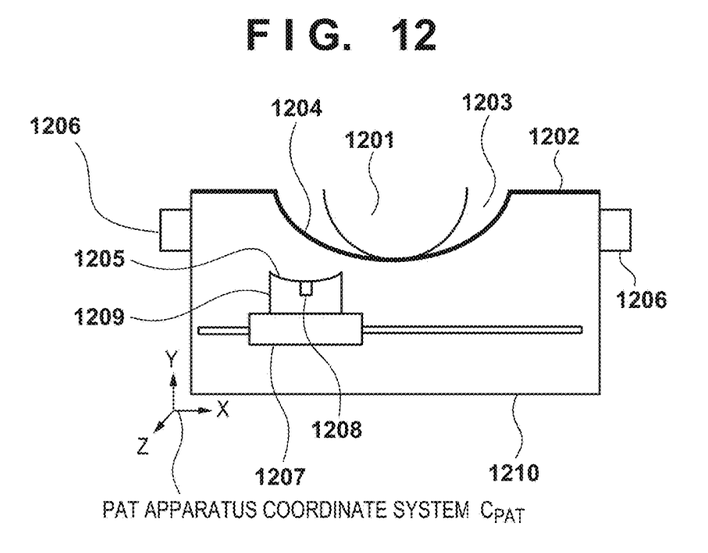
FIG. 12 is a view showing another example of the imaging apparatus according to the first embodiment.

An example of information representing directivity will be described below with reference to FIGS. 11 and 12. FIG. 11 is a view showing an example of an imaging apparatus according to this embodiment. FIG. 12 is a view showing another example of the imaging apparatus according to the embodiment. A PAT apparatus 1110 shown in FIG. 11 is a parallel plate type apparatus for holding a breast 1101 of an object 1100 inserted in an opening 1112 in such manner so as to sandwich the breast 1101 by two holding plates 1113 and 1114. A PAT apparatus 1210 shown in FIG. 12 is a holding film type apparatus for holding by a holding film 1204 a breast 1201 inserted in an opening 1203. In the PAT apparatus shown in FIG. 12, an irradiating unit 1208 performs light irradiation toward the breast 1201, and an ultrasound probe 1205 detects acoustic waves generated by the light irradiation. In the PAT apparatus shown in FIG. 12, an imaging unit 1209 that comprises the ultrasound probe 1205 and the irradiating unit 1208 can be moved by a movable stage 1207. In the PAT apparatus shown in FIG. 12, a shape measuring apparatus 1206 measures a shape of the breast 1201. When the imaging apparatus for obtaining the first image (PAT image) is a parallel plate type PAT apparatus 1110 like that shown in FIG. 11, the directivity information acquisition unit 112 may set the normal direction of a holding plate 1114 as direction information representing the direction of directivity. The directivity information acquisition unit 112 may set, for example, a value of 30° as angle information representing the strength of directivity. When the imaging apparatus for obtaining the first image (PAT image) is a holding film type PAT apparatus 1210 like that shown in FIG. 12, the directivity information acquisition unit 112 may set the normal direction of an upper surface 1202 of the PAT apparatus 1210 (or the direction of the rotation axis of an imaging unit 1209) as direction information (direction vector) representing the direction of directivity. The directivity information acquisition unit 112 may set, for example, a value of 60° as angle information representing the strength of directivity.

Note that the directivity information acquisition unit 112 may acquire a value corresponding to the position of a pixel in the first image as angle information representing the strength of directivity instead of a fixed value as described above. For example, when the imaging apparatus for the first image (PAT image) is the PAT apparatus 1210 like that shown in FIG. 12, the directivity information acquisition unit 112 may set an angle at the position of a pixel near the pectoral major muscle of a breast 1201 to an angle smaller than that at the position of a pixel near the nipple. Note that the directivity information acquisition unit 112 need not always acquire angle information representing the strength of directivity from the data server 180. For example, the directivity information acquisition unit 112 may acquire angle information input by the operator of the image processing apparatus 100 via a UI (User Interface) (not shown).

(S2020: Extraction of Target Tissue)

In step S2020, the target tissue extraction unit 114 executes the image processing of extracting an image of a target tissue (a blood vessel in this embodiment) from the second image. For example, when the pixel value of the target tissue is higher than that of a peripheral tissue, the target tissue extraction unit 114 segments the image into a high pixel value area and a low pixel value area by a discriminant analysis method or the like. In this case, the high pixel value area corresponds to the target tissue. Note that the processing of extracting an image of a target tissue from the second image may be performed by, for example, a p-tile method or known machine learning technique instead of the discriminant analysis method. Alternatively, the operator of the image processing apparatus 100 may input information about an image of the target tissue to the image processing apparatus 100 while observing a tomographic image of the second image displayed on the display unit 190. Assume that in this embodiment, the target tissue extraction unit 114 generates and holds a label image, as an image of the target tissue, with the pixel value of the target tissue having a predetermined value (for example, 1) and the pixel value of an area other than the target tissue having a value (for example, 0) other than the predetermined value. Note that when the data server 180 holds information representing an image of the target tissue, the target tissue extraction unit 114 acquires the information from the data server 180 as processing in this step.

(S2030: Registration)

In step S2030, the registration unit 116 performs registration processing between the first and second images (the processing of calculating a deformation rule to deform the second image to the first image). For registration, a known method is used, including, for example, the FFD (Free-form Deformation) method based on the corresponding points between images or image similarity or the LDDMM (Large Deformation Diffeomorphic Metric Mapping) method. In addition, if deformation between images is small or negligible (when the operator of the image processing apparatus 100 issues a corresponding instruction), the registration unit 116 calculates, as a deformation rule, coordinate transformation between the images based on linear transformation such as affine transformation or rigid-body transformation.

Note that when the data server 180 holds information about a deformation rule to deform the second image to the first image, the registration unit 116 acquires the information from the data server 180. In addition, when the data server 180 holds information to be a clue to registration, the registration unit 116 acquires the information from the data server 180, and calculates a deformation rule based on the information. For example, when having acquired the information of corresponding points as information to be a clue to registration, the registration unit 116 calculates a deformation rule based on the corresponding points.

Figure 4:
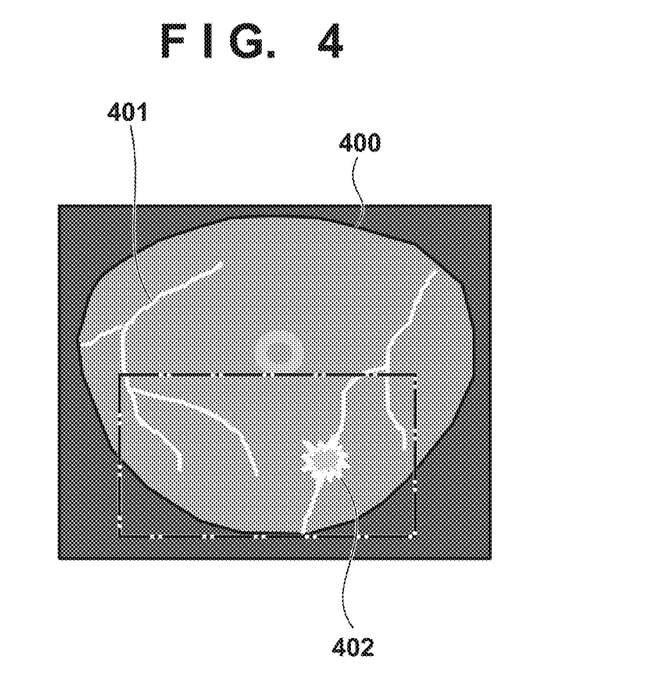
FIG. 4 is a schematic view showing an example of a deformed image of a second image according to the first embodiment.

Subsequently, the registration unit 116 deforms the second image toward the first image by using the deformation rule obtained in the above manner to generate a deformed image (a deformed MRI image in this embodiment) of the second image. FIG. 4 is a view showing a deformed image (deformed MRI image) of the second image generated by the above processing. In the deformed MRI image shown in FIG. 4, a blood vessel 401 and a tumor 402 are illustrated.

(S2040: Calculation of Direction of Target Tissue)

Figure 3:
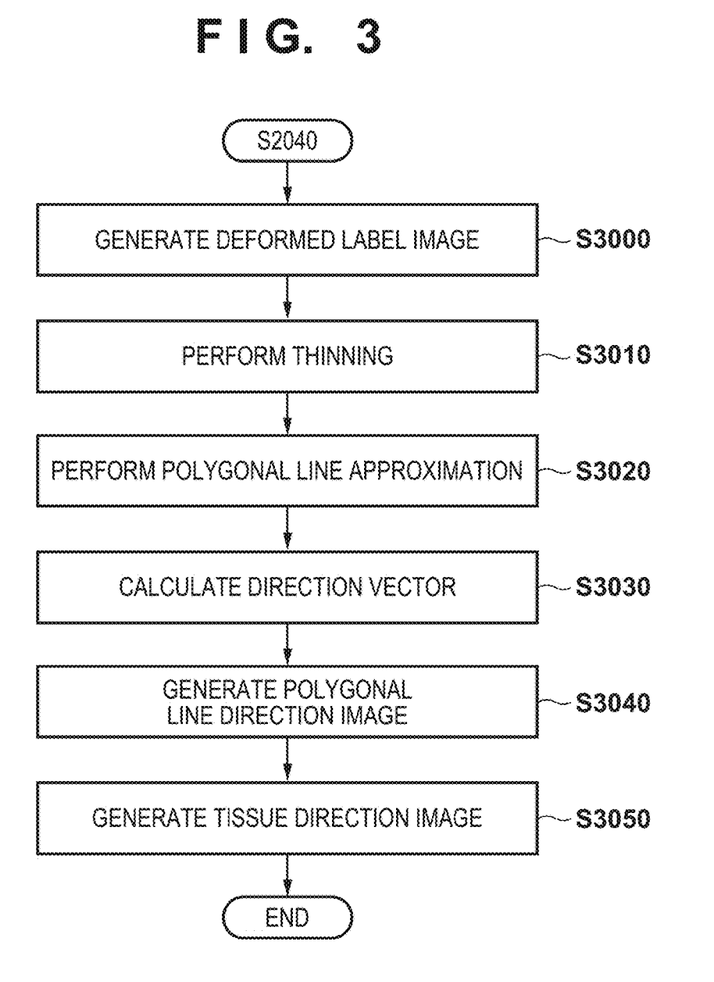
FIG. 3 is a flowchart showing a processing procedure performed by a tissue direction calculation unit 118 according to the first embodiment.

In step S2040, the tissue direction calculation unit 118 calculates information representing the direction of the target tissue based on the label image extracted in step S2020 and the deformation rule calculated in step S2030. Assume that in this embodiment, the tissue direction calculation unit 118 calculates the running direction of the blood vessel as information representing the direction of the target tissue. Processing in this step will be described in detail with reference to the flowchart of FIG. 3. FIG. 3 is a flowchart showing a processing procedure performed by the tissue direction calculation unit 118. The tissue direction calculation unit 118 generates a deformed label image by transforming the label image by using the deformation rule, and calculates information representing the direction of the target tissue based on the position of a pixel having a predetermined value in the deformed label image.

(S3000: Generation of Deformed Label Image)

In step S3000, the tissue direction calculation unit 118 generates a deformed label image by transforming the label image representing the target tissue extracted from the second image in step S2020 toward the first image.

(S3010: Thinning)

In step S3010, the tissue direction calculation unit 118 calculates a thinned pixel array by applying known thinning processing to the deformed label image of the target tissue. Alternatively, the operator of the image processing apparatus 100 may input a curve representing the central line of the target tissue to the image processing apparatus 100 while observing a tomographic image of the deformed image or deformed label image of the second image displayed on the display unit 190.

(S3020: Polygonal Line Approximation)

In step S3020, the tissue direction calculation unit 118 calculates a polygonal line approximating the pixel array by applying known vectorization processing such as a bisection method to the pixel array thinned in step S3010. Alternatively, instead of performing steps S3010 and S3020, the operator of the image processing apparatus 100 may input a polygonal line representing the central line of the target tissue to the image processing apparatus 100 while observing a tomographic image of the deformed image or deformed label image of the second image displayed on the display unit 190.

(S3030: Calculation of Direction Vector)

In step S3030, the tissue direction calculation unit 118 calculates a direction vector representing the direction of the polygonal line calculated in step S3020 for each pixel thinned in step S3010.

(S3040: Generation of Polygonal Line Image)

In step S3040, the tissue direction calculation unit 118 generates polygonal line direction images (an X-direction polygonal line image, Y-direction polygonal line image, and Z-direction polygonal line image) having the respective components of the direction vector calculated in step S3030 as pixel values.

(S3050: Generation of Tissue Direction Image)

In step S3050, with respect to a pixel whose pixel value is not set in the polygonal line image at a pixel position at which the pixel value of the deformed label image is a predetermined value (for example, 1), the tissue direction calculation unit 118 sets a pixel value at the nearest neighboring pixel position at which a pixel value is set in the polygonal line image. Tissue direction images (an X-direction image, Y-direction image, and Z-direction image) generated by the processing in this step are information representing the direction of the target tissue. In the above manner, the tissue direction calculation unit 118 executes the processing in step S2040.

(S2050: Estimation of Depicting Appearance)

Figure 5:
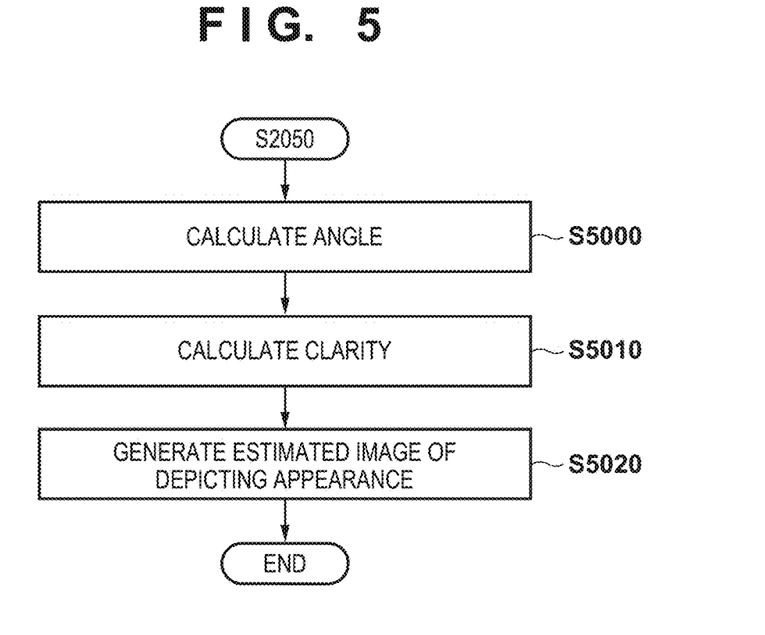
FIG. 5 is a flowchart showing a processing procedure performed by a depicting appearance estimation unit 120 according to the first embodiment.

Referring back to FIG. 2, in step S2050, the image processing apparatus 100 causes the depicting appearance estimation unit 120 to estimate a depicting appearance of the target tissue in the first image based on the relationship between the information representing the directivity acquired in step S2010 and the information representing the direction of the target tissue calculated in step S2040. The processing in this step will be described in detail below with reference to the flowchart of FIG. 5. FIG. 5 is a flowchart showing a processing procedure performed by the depicting appearance estimation unit 120 according to this embodiment. The depicting appearance estimation unit 120 calculates the clarity of depicting of the target tissue based on the information representing the directivity and the information representing the direction of the target tissue at the position of a pixel having a predetermined pixel value in the deformed label image, and estimates a depicting appearance based on the clarity and the deformed image of the second image.

(S5000: Calculation of Angle)

In step S5000, the depicting appearance estimation unit 120 calculates an angle θ defined by the direction vector representing the direction of the directivity and the direction vector representing the direction of the target tissue at each pixel position at which the pixel value of the deformed label image is a predetermined value (for example, 1). In this case, the direction vector representing the direction of the target tissue is acquired from the tissue direction image generated in step S2040.

(S5010: Calculation of Clarity)

In step S5010, the depicting appearance estimation unit 120 calculates the clarity of depicting of the target tissue at each pixel position, at which the pixel value of the deformed label image is 1, based on the angle θ calculated in step S5000 and an angle φ representing the strength of the directivity. That is, the depicting appearance estimation unit 120 generates a clarity image with a clarity being set at each pixel position. For example, when an angle obtained by subtracting θ from 90° is smaller than φ, since a target tissue is expected to be depicted, the depicting appearance estimation unit 120 sets the clarity (the degree to which the target tissue is clearly depicted) to 1. Otherwise, since no target tissue is expected to be depicted, the depicting appearance estimation unit 120 sets the clarity to 0.

Note that a clarity is not limited to a binary value of either 0 or 1, and may be set to a continuous value from 0 to 1. In this case, when an angle obtained by subtracting θ from 90° is equal to φ, it is preferable to set the clarity to 0.5. Alternatively, a table representing the relationship between each clarity and the angle difference between an angle obtained by subtracting θ from 90° and φ may be generated in advance and held in the data server 180, and the directivity information acquisition unit 112 may acquire a clarity as information concerning the strength of a directivity in step S2010. In this case, in this step, the depicting appearance estimation unit 120 may set a clarity based on this table. Note that at each pixel position at which the pixel value of a deformed label image is 0, the depicting appearance estimation unit 120 sets the pixel value of a clarity image to 0.

(S5020: Generation of Estimated Image of Depicting Appearance)

In step S5020, the depicting appearance estimation unit 120 generates an estimated image of a depicting appearance of the target tissue by multiplying the pixel value of the deformed image of the second image by the pixel value (clarity) of the corresponding clarity image. In the above manner, the depicting appearance estimation unit 120 executes the processing in step S2050.

(S2060: Setting of Display Parameters)

Referring back to FIG. 2, in step S2060, the parameter setting unit 122 sets, as display parameters for the generation of a display image, a first parameter for adjusting the pixel value of the target tissue in the deformed image of the second image and a second parameter for adjusting a transparency when superimposing the estimated image on the deformed image of the second image after adjustment with the first parameter based on inputs by the operator via the UI (not shown). More specifically, the parameter setting unit 122 sets, as the first parameter, a parameter L (0≤L≤1) for adjusting the pixel value of the target tissue in the deformed image of the second image (adjusting the easiness of discriminating the target tissue and a peripheral tissue) based on an input by the operator. In addition, the parameter setting unit 122 sets, as the second parameter, a parameter T (0≤T≤1) for adjusting a transparency when superimposing the estimated image generated in step S2050 on the deformed image of the second image after the adjustment. The processing of calculating pixel values based on these parameters will be described later in association with step S2070.

(S2070: Generation of Display Image)

In step S2070, the display image generation unit 124 generates, as a display image, an image by superimposing the target tissue with the estimated depicting appearance on the deformed image of the second image. More specifically, the display image generation unit 124 generates, as a display image, an image by superimposing the target tissue with the depicting appearance estimated in step S2050 on a tomographic image of the deformed image of the second image which is cut along a cutting plane set by the operator. At this time, the display image generation unit 124 generates a display image based on the first parameter (L) and the second parameter (T) obtained in step S2060. More specifically, first of all, based on the parameter L set in step S2060, the display image generation unit 124 changes a pixel value I2 of the target tissue in the deformed image of the second image to a pixel value I2' according to the following equation.

$$I2' = IS + L \cdot (I2 - IS) \quad (1)$$

where IS a representative pixel value of a tissue (to be referred to as a peripheral tissue hereinafter) existing around the target tissue. For example, as this value, the average value of pixel values circumscribed to a contour of the target tissue can be used. In this case, when the parameter L is 1, the pixel value of the target tissue is not changed from I2. In contrast, when the parameter L is 0, the pixel value I2' of the target tissue coincides with a representative pixel value IS of the peripheral tissue (the target tissue is displayed with a depicting appearance that does not allow discrimination from the peripheral tissue).

Subsequently, based on the parameter T set in step S2060, the display image generation unit 124 calculates a pixel value I2" of the display image at each pixel position at which the pixel value of the deformed label image is 1 according to the following equation. Note that at each pixel position at which the pixel value of the deformed label image is 0, the display image generation unit 124 may set the pixel value I2 in the deformed image of the second image as the pixel value I2" of the display image without any change.

$$I2''=T \cdot IE+(1-T) \cdot I2' \quad (2)$$

where IE represents the pixel value of the estimated image generated in step S2050. According to this equation, the pixel value IE of the estimated image is combined with the pixel value I2' in the deformed image of the second image having undergone the above change. In this case, when the parameter T is 1, the pixel value I2' of the target tissue in the deformed image of the second image is overwritten with the pixel value IE of the estimated image. On the other hand, when the parameter T is 0, the pixel value IE in the estimated image is not displayed.

Note that the display image generation unit 124 may calculate the pixel value I2" of the display image based on the clarity calculated in step S5010 instead of generating an estimated image of a depicting appearance of the target tissue and superimposing it on the deformed image of the second image. For example, the display image generation unit 124 may calculate the pixel value I2" of the display image by multiplying the pixel value I2 of the deformed image of the second image by the clarity calculated in step S5010 at each pixel position at which the pixel value of the deformed label image is 1. In this case, it is not necessary to execute the processing in steps S5020 and S2060.

(S2080: Display of Image)

Figure 6:
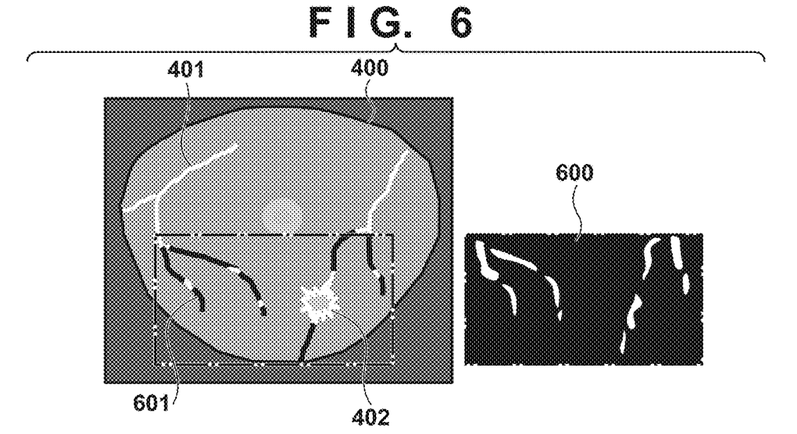
FIG. 6 is a schematic view showing an example of an image generated by the image processing apparatus according to the first embodiment.
Figure 7:
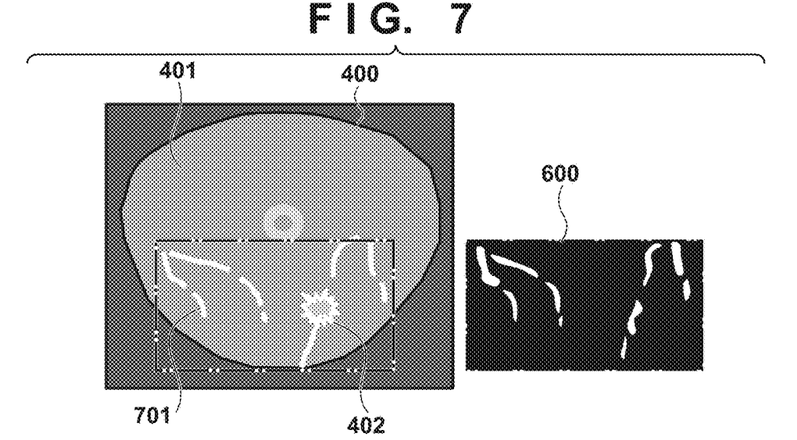
FIG. 7 is a schematic view showing another example of the image generated by the image processing apparatus according to the first embodiment.

Referring back to FIG. 2, in step S2080, the display control unit 126 performs control to display the display image generated in step S2070 on the display unit 190. FIGS. 6 and 7 each show an example of an image displayed by the above processing.

FIG. 6 shows a display image when the parameter L is 1 and the parameter T is 0.5. In this case, a translucent image of the blood vessel (target tissue) is superimposed, with an estimated depicting appearance (a superimposed blood vessel 601), on a tomographic image of a deformed MRI image (a deformed image of the second image) 400. FIG. 6 shows a display example of displaying a corresponding PAT image (first image) 600 next to the above image.

FIG. 7 shows a display image when the parameter L is 0 and the parameter T is 1. In this case, the blood vessel (target tissue) in a tomographic image of the deformed MRI image (the deformed image of the second image) 400 is displayed with a depicting appearance (an extracted blood vessel 401) that does not allow discrimination from the peripheral tissue. In addition, the blood vessel (target tissue) is overwritten (a blood vessel 701 with an estimated image extraction depicting appearance), with an estimated depicting appearance, on the tomographic image. FIG. 7 also shows a display example of displaying the corresponding PAT image (first image) 600 next to the above image.

(S2090: Determination of Change in Displaying Appearance)

In step S2090, the image processing apparatus 100 determines whether the operator has input an instruction to change the displaying appearance (to reset display parameters) via the UI (not shown). For example, the image processing apparatus 100 acquires an instruction to change which the operator has input by, for example, pressing predetermined keys of the keyboard. If the image processing apparatus 100 determines that the displaying appearance is changed, the process returns to step S2060 to execute display parameter resetting processing. If the image processing apparatus 100 determines that the displaying appearance is not changed, the process advances to step S2100.

(S2100: Determination of End)

In step S2100, the image processing apparatus 100 determines whether to terminate the overall processing. For example, the image processing apparatus 100 acquires an end instruction which the operator has input by, for example, pressing a predetermined key (end key) of the keyboard. Upon determining to terminate the overall processing, the image processing apparatus 100 terminates the processing. Upon determining not to terminate the overall processing, the image processing apparatus 100 returns the process to step S2070 to repeatedly execute the processing of displaying a display image in accordance with a new cutting plane set by the operator. In the above manner, the image processing apparatus 100 executes processing.

As described above, the image processing apparatus according to this embodiment estimates the depicting appearance of a target tissue in the first image (target image) based on information representing the direction of the target tissue in the second image (reference image), and displays the target tissue on the second image (reference image) with the estimated depicting appearance. Performing estimation processing and display processing based on a target tissue in this manner can properly estimate the depicting appearance of the target tissue in the first image (target image) and display the target tissue on the second image (reference image) with high visibility.

(First Modification)

Although the first embodiment has exemplified the case in which the target tissue is the blood vessel, the target tissue is not limited to the blood vessel. For example, the target tissue may be the mammary gland or body surface of an object. When the target tissue is the mammary gland of the object, processing similar to that for the blood vessel may be performed. If the target tissue is the body surface of the object, the tissue direction calculation unit 118 may calculate the normal direction of the body surface as information representing the direction of the target tissue in step S2040. In step S5010, the depicting appearance estimation unit 120 may set the estimated value to 1 when θ is smaller than φ, and set the estimated value to 0 in other cases.

(Second Modification)

Although the first embodiment has exemplified the case in which the object is the breast, the object is not limited to the breast, and may be an arbitrary organ such as the heart, liver, lung, or brain.

(Third Modification)

Although the first embodiment has exemplified the case in which the target image (first image) is a PAT image (an image obtained by a PAT apparatus), the target image is not limited to a PAT image. For example, the target image may be an image obtained by an ultrasonic diagnostic apparatus or an image obtained by an X-ray mammography apparatus.

(Fourth Modification)

The first embodiment has exemplified the case in which the reference image (second image) is an MRI image (an image obtained by an MRI apparatus), the reference image is not limited to an MRI image. For example, the reference image (second image) may be a CT image (an image obtained by an X-ray CT apparatus) or a three-dimensional ultrasonic image obtained by an ultrasonic diagnostic apparatus. Alternatively, the reference image (second image) may be an image obtained by a tomosynthesis apparatus.

(Fifth Modification)

When the first and second images are registered in advance (images are registered in advance such that there are no differences between the images in terms of coordinate system and deformed state, and the same coordinates represent the same places), the processing in step S2030 can be omitted. For example, this operation corresponds to a case in which a three-dimensional ultrasonic image obtained by a hybrid apparatus, which can simultaneously obtain an ultrasonic image and a PAT image, and a PAT image are displayed. In this case, the position of the target tissue obtained from a three-dimensional ultrasonic image can be directly regarded as the position of the target tissue in a PAT image. The processing for the deformed image of the second image from step S2040 can be replaced with processing for the second image.

(Second Embodiment)

An image processing apparatus according to the second embodiment is featured to correct a target image (PAT image) based on the result of estimating the depicting appearance of a target tissue in the target image (PAT image). The image processing apparatus according to this embodiment will be described below concerning differences from the first embodiment.

The arrangement of an image processing system 1, the operation of each unit of an image processing apparatus 100, and processing procedures according to this embodiment are almost the same as those according to the first embodiment. Note however that processing from step S2060 to step S2080 differs from that in the first embodiment. The processing from step S2060 to step S2080 will be described below.

(S2060: Setting of Display Parameter)

In step S2060, a parameter setting unit 122 sets a display parameter for the generation of a display image based on an input by the operator via a UI (not shown). More specifically, the parameter setting unit 122 sets, based on an input by the operator, a parameter C ($0 \leq C \leq 1$) for the correction of the pixel value of a region corresponding to a target tissue in the first image based on an estimated image generated in step S2050. This parameter is used to adjust the degree of correction. The processing of changing a pixel value based on this parameter will be described with reference to step S2070 to be described later.

(S2070: Generation of Display Image)

In step S2070, a display image generation unit 124 corrects the pixel value of the region corresponding to the target tissue in the first image based on an estimated depicting appearance, and generates the corrected image as a display image. More specifically, the display image generation unit 124 corrects the pixel value of the region corresponding to the target tissue in a tomographic image of the first image which is cut along a cutting plane set by the operator based on the estimated image generated in step S2050, and generates the corrected image as a display image. At this time, the display image generation unit 124 uses the display parameter obtained in step S2060. More specifically, based on the parameter C set in step S2060, the display image generation unit 124 calculates a pixel value $I1'$ of the display image by changing a pixel value $I1$ of the region corresponding to the target tissue in the tomographic image of the first image according to the following equation.

$$I1' = IE + C \cdot (I1 - IE) \quad (3)$$

In this case, when the parameter C is 1, the pixel value $I1$ of the target tissue is not changed. When the parameter C is 0, the pixel value of the target tissue coincides with a pixel value EI of the estimated image of the target tissue (the pixel value of the target tissue is replaced with the pixel value IE of the estimated image).

Note that the display image generation unit 124 may calculate the pixel value $I1'$ of the display image based on the clarity calculated in step S5010 instead of generating an estimated image of the depicting appearance of the target tissue and correcting the region corresponding to the target tissue in the first image. For example, the display image generation unit 124 may calculate the pixel value $I1'$ of the display image by multiplying the pixel value $I1$ of the region corresponding to the target tissue in the first image by the reciprocal of the clarity at each pixel position at which the pixel value of the deformed label image is 1. In this case, if the clarity is equal to or less than a threshold, the display image generation unit 124 may multiply the pixel value $I1$ by the reciprocal of the threshold instead of the reciprocal of the clarity. In this case, it is not necessary to execute the processing in steps S5020 and S2060.

(S2080: Display of Image)

Figure 8:
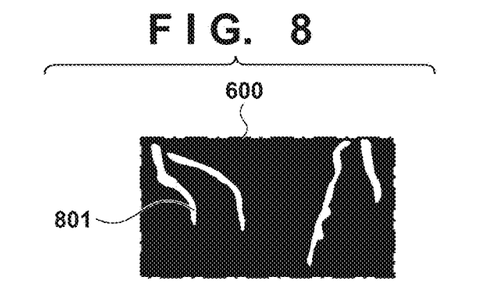
FIG. 8 is a schematic view showing an example of an image generated by an image processing apparatus according to the second embodiment.

In step S2080, a display control unit 126 performs control to display the display image generated in step S2070 on a display unit 190. FIG. 8 shows an example of an image displayed by the above processing. FIG. 8 shows a tomographic image of the first image (PAT image) when the parameter C is 0.5. In a PAT image 800 in FIG. 8, a corrected vessel 801 is illustrated.

As described above, the image processing apparatus according to this embodiment estimates the depicting appearance of a target tissue in the first image (target image) based on information representing the direction of the target tissue in the second image (reference image). The image processing apparatus then corrects the pixel value of a region corresponding to the target tissue in the first image (target image) based on the estimated depicting appearance. Performing such processing makes it possible to display the target tissue in the first image (target image) upon properly correcting a defective portion of the target tissue. In addition, this correction can suppress variations in the depicting appearance of the target tissue (blood vessel) in a PAT image, and hence can improve the quantitative property of the PAT image.

Note that this embodiment has exemplified the case in which the image processing apparatus corrects the pixel value of a region corresponding to a target tissue in the first image (target image) based on an estimated depicting appearance. However, a deriving unit (not shown) may obtain information for supporting diagnosis based on an estimated depicting appearance. For example, the image processing apparatus may generate an image by superimposing a target tissue on the first image with an estimated depicting appearance, and present the resultant image to the operator, thereby allowing the operator to easily determine whether a tissue depicted on the first image is a target tissue or noise.

(Third Embodiment)

An image processing apparatus according to the third embodiment is featured to improve registration accuracy by repeatedly estimating the depicting appearance of a target tissue in a target image (PAT image) and updating a deformation rule to deform the second image to the first image based on the estimation result. The image processing apparatus according to this embodiment will be described below concerning differences from the first embodiment.

Figure 9:
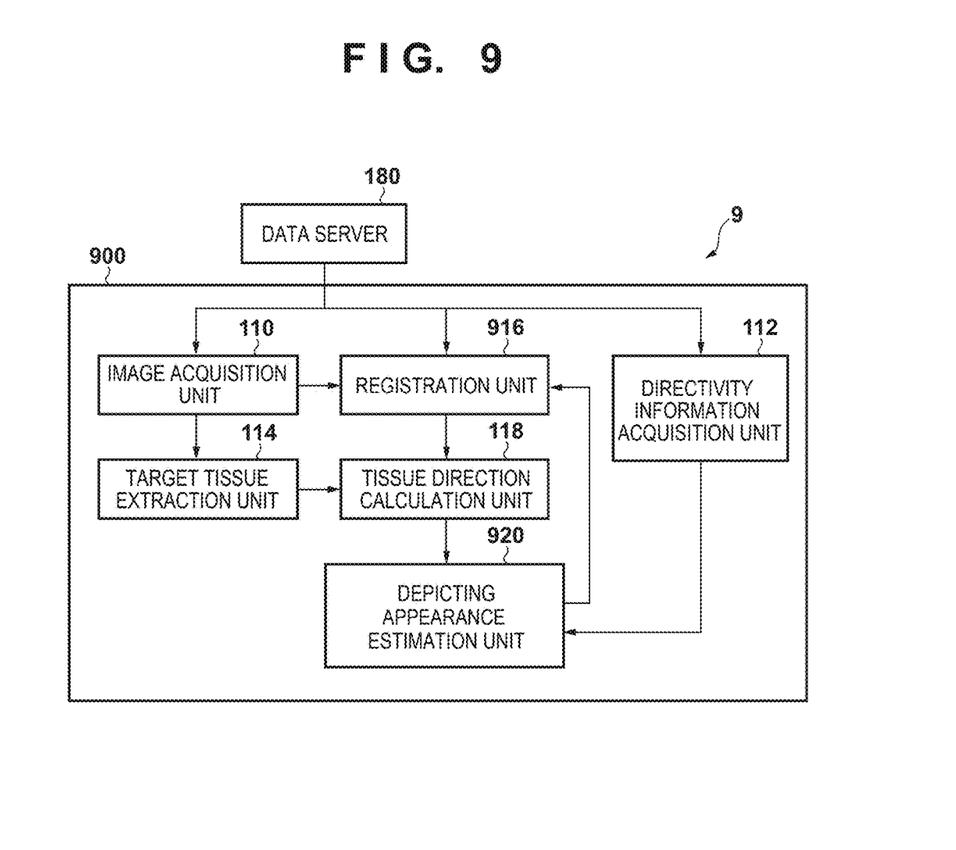
FIG. 9 is a block diagram showing the functional arrangements of an image processing system and an image processing apparatus according to the third embodiment.

FIG. 9 shows the arrangement of an image processing system 9 according to this embodiment. The same reference numerals and symbols as those in FIG. 1 denote the same parts, and a description of them will be omitted.

An image processing apparatus 900 includes an image acquisition unit 110, a directivity information acquisition unit 112, a target tissue extraction unit 114, a registration unit 916, a tissue direction calculation unit 118, and a depicting appearance estimation unit 920. The image processing apparatus 900 is connected to a data server 180. The registration unit 916 calculates a deformation rule to deform the second image to the first image based on the result of estimating the depicting appearance of a target tissue (performs registration). The depicting appearance estimation unit 920 estimates the displaying appearance of the extracted target tissue based on the relationship between the registration result, information representing the direction of the target tissue, and information representing directivity.

Figure 10:
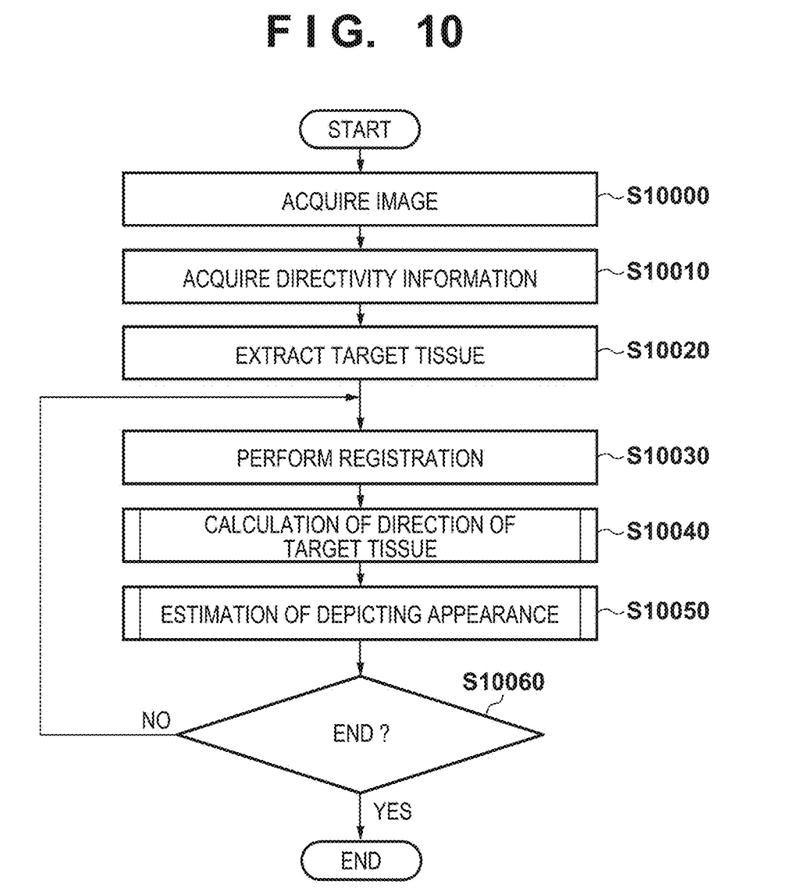
FIG. 10 is a flowchart showing a processing procedure performed by the image processing apparatus according to the third embodiment.

FIG. 10 is a flowchart showing a processing procedure executed by an image processing apparatus 100 according to this embodiment. Processing in steps S10000, S10010, S10020, S10040, and S10050 is the same as that in steps S2000, S2010, S2020, S2040, and S2050 in the first embodiment, and a description of it will be omitted. Processing in steps S10030 and S10060 will be described below.

(S10030: Registration)

In step S10030, the registration unit 916 performs registration processing between the first and second images (the processing of calculating a deformation rule to deform the second image to the first image). In the registration processing according to this embodiment, the registration unit 916 acquires information about corresponding points as information as a clue to registration, and executes the registration processing based on the corresponding points. In this case, when executing processing in this step after step S10060, the registration unit 916 updates the deformation rule to deform the second image to the first image based on the depicting appearance of the target tissue estimated in step S10050. For example, the registration unit 916 handles the clarity calculated in step S5010 in step S10050 as the reliability of information as a clue to registration. When executing registration processing based on the corresponding points, the registration unit 916 updates the deformation rule to deform the second image to the first image by performing a weighting operation in accordance with the reliability.

In this case, in a stage in which the number of times of repetition of registration is small, the directivity information acquisition unit 112 may set angle information representing the strength of directivity to a value smaller than it really is, and the registration unit 916 may perform registration based on reliably associated information. In this case, the directivity information acquisition unit 112 brings angle information representing the angle of directivity nearer to an actual value in accordance with the number of times of repetition of registration. This allows the registration unit 916 to finally perform registration with higher accuracy.

(S10100: Determination of End)

In step S10100, the image processing apparatus 900 determines whether to terminate the overall processing. Upon determining to terminate the overall processing, the image processing apparatus 900 causes the image processing apparatus 100 to terminate processing. In contrast to this, if the image processing apparatus 100 does not determine the end of the processing, the process returns to step S10030 to update the deformation rule to deform the second image to the first image. In the above manner, the image processing apparatus 900 executes processing.

As described above, the image processing apparatus according to this embodiment repeatedly estimates the depicting appearance of a target tissue in a target image (PAT image) and updates the deformation rule to deform the second image to the first image based on the estimation result. Performing this processing can improve the accuracy of registration.

(First Modification)

The third embodiment has exemplified the case in which the processing does not proceed to the generation of a display image. However, the processing may proceed to the generation of a display image as in the first embodiment. According to this modification, like the image processing apparatus 100, the image processing apparatus 900 further includes a parameter setting unit 122, a display image generation unit 124, and a display control unit 126. In addition, the image processing apparatus 900 executes processing from step S2060 to step S2090. In this case, in step S10030, the operator can update the information of corresponding points based on the depicting appearance of the target tissue which is estimated in step S10050. The registration unit 916 then executes registration processing based on the updated corresponding points. Alternatively, the registration unit 916 can execute known image-based registration processing based on a display image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-156241, filed Aug. 6, 2015, which is hereby incorporated by reference herein in its entirety.

What is claimed is:

1. An image processing apparatus comprising:
an acquisition unit configured to acquire information representing directivity at the time of imaging a first image of an object obtained by a first apparatus;

a calculation unit configured to calculate information representing a direction of a target tissue based on an image of the target tissue in a second image of the object obtained by a second apparatus;

a registration unit configured to (1) acquire a deformation rule to deform the second image to the first image as registration information for registration between the first image and the second image and (2) generate a deformed image of the second image by performing deforming the second image toward the first image by using the deformation rule as the registration between the first image and the second image;

an extracting unit configured to generate a label image by extracting an image representing the target tissue from the second image;

an estimation unit configured to estimate a depicting appearance of the target tissue in the first image based on (1) the information representing the directivity and (2) the information representing the direction of the target tissue; and an image generation unit configured to generate a display image based on the depicting appearance of the target issue in the first image, wherein the calculation unit generates a deformed label image by transforming the label image by using the deformation rule, and calculates the information representing the direction of the target tissue based on the deformed label image, and wherein the image generation unit is configured to generate, as the display image, an image by superimposing (a) the deformed image of the second image and (b) an image of the target tissue with the depicting appearance of the target tissue in the first image.

2. The apparatus according to claim 1, wherein the estimation unit is configured to calculate a clarity of depicting of the target tissue based on the information representing the directivity and the information representing the direction of the target tissue in the deformed label image, and to estimate the depicting appearance based on the clarity and the deformed image of the second image.

3. The apparatus according to claim 1, wherein the registration unit is configured to calculate the deformation rule based on the depicting appearance of the target tissue in the first image.

4. The apparatus according to claim 1, wherein the extracting unit is configured to generate the label image with a pixel value of the target tissue being a predetermined value and a pixel value other than the target tissue being a value other than the predetermined value, wherein the apparatus further comprises a setting unit configured to set a first parameter for adjusting the pixel value of the target tissue in the deformed image of the second image and a second parameter for adjusting a transparency when superimposing the image of the target tissue with the depicting appearance of the target tissue on the deformed image of the second image after adjustment using the first parameter, and wherein the display image generation unit is configured to generate the display image based on the first parameter and the second parameter.

5. The apparatus according to claim 1, wherein the display image generation unit is configured to correct a pixel value of a region corresponding to a defective portion of the target tissue in the first image based on the depicting appearance of the target tissue in the first image, and generates the corrected image as the display image.

6. The apparatus according to claim 1, further comprising a deriving unit configured to obtain information for supporting diagnosis of the first image based on the depicting appearance of the target tissue in the first image.

7. The apparatus according to claim 1, wherein the first apparatus comprises a Photo Acoustic Tomography apparatus, and the second apparatus comprises a Magnetic Resonance Imaging apparatus.

8. The apparatus according to claim 1, wherein the target tissue is a blood vessel.

9. The apparatus according to claim 1, wherein the image generation unit is configured to determine a displaying appearance of the deformed image of the second image based on the depicting appearance of the target tissue in the first image, and to generate, as the display image, the deformed image of the second image with the displaying appearance.

10. The apparatus according to claim 1, further comprising a parameter setting unit configured to set a display parameter based on the depicting appearance of the target tissue in the first image, wherein the image generation unit is configured to generate the display image from the first image and the deformed image of the second image based on the display parameter.

11. The apparatus according to claim 1, further comprising a display control unit configured to cause a display unit to display the display image.

12. The apparatus according to claim 1, wherein the extracting unit is configured to generate the label image with a pixel value of the target tissue being a predetermined value and a pixel value other than the target tissue being a value other than the predetermined value, and wherein the calculation unit is configured to calculate the information representing the direction of the target tissue based on a position of the pixel having the predetermined value in the deformed label image.

13. The apparatus according to claim 1, wherein the extracting unit is configured to generate the label image by extracting the image representing the target tissue from the second image using a machine learning technique.

14. An image processing method comprising:

acquiring information representing directivity at the time of imaging a first image of an object obtained by a first apparatus;

calculating information representing a direction of a target tissue based on an image of the target tissue in a second image of the object obtained by a second apparatus;

acquiring a deformation rule to deform the second image to the first image as registration information for registration between the first image and the second image;

generating a deformed image of the second image by performing deforming the second image toward the first image by using the deformation rule as the registration between the first image and the second image;

generating a label image by extracting an image representing the target tissue from the second image;

generating a deformed label image by transforming the label image by using the deformation rule;

estimating a depicting appearance of the target tissue in the first image based on (1) the information representing the directivity and (2) the information representing the direction of the target tissue; and generating a display image based on the depicting appearance of the target tissue in the first image, wherein the information representing the direction of the target tissue is calculated based on the deformed label image, and wherein an image is generated as the display image, by superimposing (a) the deformed image of the second image and (b) an image of the target tissue with the depicting appearance of the target tissue in the first image.

15. A non-transitory computer-readable storage medium storing a computer program for causing a computer to execute an image processing method, the image processing method comprising:

acquiring information representing directivity at the time of imaging a first image of an object obtained by a first apparatus;

calculating information representing a direction of a target tissue based on an image of the target tissue in a second image of the object obtained by a second apparatus;

acquiring a deformation rule to deform the second image to the first image as registration information for registration between the first image and the second image;

generating a deformed image of the second image by performing deforming the second image toward the first image by using the deformation rule as the registration between the first image and the second image;

generating a label image by extracting an image representing the target tissue from the second image;

generating a deformed label image by transforming the label image by using the deformation rule;

estimating a depicting appearance of the target tissue in the first image based on (1) the information representing the directivity and (2) the information representing the direction of the target issue; and generating a display image based on the depicting appearance of the target tissue in the first image, wherein the information representing the direction of the target tissue is calculated based on the deformed label image, and wherein an image is generated as the display image, by superimposing (a) the deformed image of the second image and (b) an image of the target tissue with the depicting appearance of the target tissue in the first image.

16. The image processing method according to claim 15, wherein the label image with a pixel value of the target tissue being a predetermined value and a pixel value other than the target tissue being a value other than the predetermined value, is generated, and wherein the information representing the direction of the target tissue is calculated based on a position of the pixel having the predetermined value in the deformed label image.

17. The image processing method according to claim 15, wherein the label image is generated by extracting the image representing the target tissue from the second image using a machine learning technique.

* * * * *